(12) United States Patent
Bush et al.

(10) Patent No.: US 6,372,716 B1
(45) Date of Patent: Apr. 16, 2002

(54) FORMULATIONS FOR FACTOR IX

(75) Inventors: Lawrence Bush, Tewksbury, MA (US); Chandra Webb, Pelham, NH (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 08/233,663

(22) Filed: Apr. 26, 1994

(51) Int. Cl.$^7$ ................................................ A61K 38/36
(52) U.S. Cl. ........................... 514/8; 530/381; 530/384
(58) Field of Search ................................ 530/381, 384; 514/8

(56) References Cited

U.S. PATENT DOCUMENTS

| | | | |
|---|---|---|---|
| 4,405,603 A | * 9/1983 | Schwinn et al. | 424/101 |
| 4,470,968 A | * 9/1984 | Mitra et al. | 424/101 |
| 4,495,278 A | 1/1985 | Thomas | 435/5 |
| 4,540,573 A | * 9/1985 | Neurath et al. | 424/85 |
| 4,597,966 A | * 7/1986 | Zolton et al. | 424/85 |
| 4,770,999 A | 9/1988 | Kaufman et al. | 435/68 |
| 4,877,608 A | 10/1989 | Lee et al. | 424/85.8 |
| 4,952,675 A | * 8/1990 | Mathews et al. | 530/383 |
| 5,288,853 A | * 2/1994 | Bhattacharva et al. | 530/383 |
| 5,457,181 A | 10/1995 | Michalski et al. | |
| 5,565,427 A | 10/1996 | Freudenberg | |

FOREIGN PATENT DOCUMENTS

DE 4001451 * 8/1991

OTHER PUBLICATIONS

Arakawa et al., Pharm Res, vol. 8(3), pp. 285–291, 1991.*
"Protein Structures", a practical approach, Ed.*
T. E. Creighton, IRL Press, Chap 14, 1989.*
Pikal et al., Biopharm, vol. 3(9), pp. 26–30, 1990.*
Wang et al., J. Parenteral Sci & Tech., vol. 42, No. 2s, pp. s3–s26, 1988.*
MacLeod, et al., Scottish National Blood Tranfusion Service, Research Disclosure 24427 (1984).
Choo et al., Nature 299:178–180 (1982).
Fair et al., Blood 64:194–204 (1984).
Kurachi et al., PNAS 79:6461–6464 (1982).
Manning et al., Pharm. Res. 6:903–918 (1989).
Hrinda et al., Seminars in Hematology 28:6–14 (1991).
Tharakan et al., J. Chrom. 595:103–111 (1992).
Liebman et al., PNAS 82:3879–3883 (1985).
Hashimoto et al., J. Biochem. 97:1347–1355 (1985).
Bajaj et al., Prep. Biochem. 11(4):397–412 (1981).
Pittman et al., Blood 79:389–397 (1992).
Alpha Therapeutics Corporation, Coagulation Factor IX (Human) AlphaNine SD Affinity Purified Solvent Detergent Treated:pp. 1–4 (1992).

* cited by examiner

Primary Examiner—Chhaya D. Sayala
(74) Attorney, Agent, or Firm—Albert Ubieta

(57) ABSTRACT

Provided by the present invention are novel compositions and methods for obtaining concentrated preparations of factor IX and formulations of factor IX suitable for storage and administration.

12 Claims, No Drawings

FORMULATIONS FOR FACTOR IX

FIELD OF INVENTION

The present invention relates generally to novel formulations comprising factor IX.

BACKGROUND OF INVENTION

A variety of factors involved in the blood clotting process have been identified, including factor IX, a plasma glycoprotein. A deficiency of factor IX characterizes a type of hemophilia (type B). Treatment of this disease has traditionally involved intra venous infusion of human plasma-derived protein concentrates of factor IX. Infusion of blood concentrates involves the risk of transmission of various infectious agents, such as viral hepatitis and HIV, or thromboembolic factors. An alternative method of producing factor IX, by recombinant DNA techniques, has been described in U.S. Pat. No. 4,770,999, Kaufman et al., Sep. 13, 1988. The cDNA coding for human factor IX has been isolated, characterized, and cloned into expression vectors. See, for example, Choo et al., Nature 299:178–180 (1982); Fair et al., Blood 64:194–204 (1984); and Kurachi et al., Proc. Natl. Acad. Sci., U.S.A. 79:6461–6464 (1982). Thus, through advances in recombinant DNA technology, it has been possible to produce factor IX protein.

It is desirable to have concentrated forms of bulk protein, e.g., factor IX, which, in turn, may be stored and which are suitable for further manufacture of finished dosage forms of protein. Typically, a purification process for a protein results in concentrating the protein. This concentrated protein, also known as bulk protein, may be in a formulation buffer. Bulk protein, typically at a concentration of about 2 to at least 20 mg/ml, can then be shipped frozen to a fill/finish facility where it is diluted to an appropriate dosage concentration and placed into dosage vials. These diluted samples can be lyophilized, i.e., freeze-dried. The lyophilized samples may be kept in long-term storage and reconstituted at a later time by adding a suitable administration diluent just prior to patient use.

Protein stability can be affected inter alia by such factors as ionic strength, pH, temperature, repeated cycles of freeze/thaw and exposures to shear forces. Active protein may be lost as a result of physical instabilities, including denaturation and aggregation (both soluble and insoluble aggregate formation), as well as chemical instabilities, including, for example, hydrolysis, deamidation and oxidation, to name just a few. For a general review of stability of protein pharmaceuticals, see, for example, Manning, et al., Pharmaceutical Research 6:903–918 (1989).

While the possible occurrence of protein instabilities is widely appreciated, it is impossible to predict particular instability problems of a particular protein. Any of these instabilities can result in the formation of a protein, protein by-product, or derivative having lowered activity, increased toxicity, and/or increased immunogenicity. Indeed, protein precipitation may lead to thrombosis, non-homogeneity of dosage form and amount, as well as clogged syringes. Also, specific to factor IX, there are several post-translational modifications (for example, the gamma carboxylation of certain glutamic acid residues in the N-terminus and the addition of carbohydrate) which may be important in maintaining biological activity and which may be susceptible to modification upon storage. Thus, the safety and efficacy of any pharmaceutical formulation of a protein is directly related to its stability.

In addition to stability considerations, one generally selects excipients which are or will meet with the approval of various world-wide medical regulatory agencies. The solution should be isotonic and the pH in a physiologically suitable range. The choice and amount of buffer used is important to achieve the desired pH range. Moreover, in the case of factor IX, agents such as "heparin" are to be avoided because of potential interference with clotting time assay analysis and with accurate assessment of thrombogenic potential.

Currently, there are only two commercially available, carrier-protein-free, plasma-derived factor IX formulations. Alpha Therapeutic Corporation provides lyophilized Alpha-Nine® SD: comprising heparin, dextrose, polysorbate 80, and tri(n-butyl) phosphate. This preparation is meant to be stored at temperatures between 2° and 8° C. As noted supra, heparin is to be avoided as it is an anti-coagulant and tri(n-butyl) phosphate is irritating to mucous membranes; thus, this formulation is less than ideal. Armour Pharmaceutical Company's lyophilized Mononine®: comprising histidine, sodium chloride and mannitol is similarly meant to be stored at 2° to 8° C. The package insert recommends not storing this formulation for greater than one month at room temperature.

Ideally, formulations developed should also be stable for factor IX bulk storage in high concentration ($\leq 20$ mg/ml, for example) which allows for relatively small volumes for fill/finish at the appropriate dose and also allows for alternate methods of administration which may require high protein concentration, e.g., sub cutaneous administration. Accordingly, there continues to exist a need in the art for methods for improving factor IX protein stability (and maintaining activity levels) during the concentration process, and the lyophilization process, as well as providing stable formulations during prolonged storage.

BRIEF SUMMARY OF THE INVENTION

One aspect of the present invention provides novel compositions and methods for providing concentrated preparations of factor IX, useful as bulk drug product. These compositions, either frozen, liquid, or lyophilized, comprise factor IX, a bulking agent, such as glycine, and a cryoprotectant. A preferred factor IX concentration ranges from about 0.1 to at least 20 mg/ml (equivalent to about 20 to at least 4000 U/ml). Preferred bulking agents include glycine, and/or a magnesium, calcium, or chloride salt, preferably ranging in concentration from about 0.5 to 300 mM. Suitable cryoprotectants include polyols, such as mannitol and sucrose, and preferably range in concentration from about 0.5 to 2%. Optionally, these bulk drug product compositions may also contain a surfactant or detergent, such as polysorbate (e.g., Tween-80) or polyethyleneglycol (PEG), which may also serve as a cryoprotectant during the freezing step. The surfactant preferably ranges from about 0.005 to 0.05%. Preferably, the concentrations of the excipients provide a combined osmolality of about 250 to 350 milliosmolal (mOsM), preferably about 300 mOsM±50 mOsM, and further, may contain an appropriate buffering agent to maintain a physiologically suitable pH e.g., in the range preferably of about 6.0 to 8.0. Buffering agents preferably include histidine, and sodium or potassium phosphate, with a target pH of about 6.5 to 7.5, all at about 5–50 mM.

Another aspect of the present invention provides formulations of factor IX suitable for administration in a final dosage form, for example, via intra venous or sub cutaneous injection. Preferred formulations include factor IX concentrations ranging from about 0.1 to at least 20 mg/ml, about 0.5 to 2% sucrose, about 0.1 to 0.3 M glycine, and about 0.005% to 0.02% polysorbate, with histidine as a buffering agent, ranging from about 5 to 50 mM. A preferred lyophilized formulation comprises about 0.1 to at least 10 mg/ml factor IX, about 260 mM glycine, about 1% sucrose, about 0.005% polysorbate, and about 10 mM histidine, at pH 7.0.

DETAILED DESCRIPTION OF THE INVENTION

As used herein, the terms lyophilization, lyophilized, and freeze-dried include but are not limited to processes including "freezing" a solution followed by "drying", optionally in vacuo. As used herein, the term "bulking agent" comprises agents which provide good lyophilized cake properties, which help the protein overcome various stresses (shear/freezing for example) associated with the lyophilization process, and which help to maintain protein activity levels. Exemplary bulking agents include, but are not limited to, glycine, $MgCl_2$, $CaCl_2$, NaCl, and the like. These agents contribute to the tonicity of the formulations. Cryoprotectants also contribute to the tonicity. The term "cryoprotectants" generally includes agents which provide stability to the protein from freezing-induced stresses; however, the term also includes agents that provide stability, e.g., to bulk drug formulations during storage from non-freezing-induced stresses. Exemplary cryoprotectants include polyols, and include saccharides such as sucrose and mannitol, as well as including surfactants such as polysorbate, or polyethyleneglycol, and the like. The term "lyoprotectant" includes agents that provide stability to the protein during water removal from the system during the drying process, presumably by maintaining the proper conformation of the protein through hydrogen bonding. Cryoprotectants can also have lyoprotectant effects. While preferred concentrations of cryoprotectant range from about 0.5 to 2%, relatively high concentrations, for example 5%, are suitable with the levels used limited only by those customarily used in clinical practice.

"Surfactants" generally include those agents which protect the protein from air/solution interface induced stresses and solution/surface induced stresses (e.g., resulting in protein aggregation), and may include detergents such as polysorbate-80 (Tween), for example, 0.005–0.05% (weight/volume), or polyethyleneglycol (PEG), such as PEG8000, for example. Optionally, relatively high concentrations, e.g., up to 0.5%, are suitable for maintaining protein stability; however, the levels used in actual practice are customarily limited by clinical practice.

The term "buffering agent" encompasses those agents which maintain the solution pH in an acceptable range prior to lyophilization and may include histidine, phosphate (sodium or potassium), tris(tris(hydroxymethyl) aminomethane), diethanolamine, and the like. The upper concentration limits are generally higher for "bulk" protein than for "dosage" protein forms as is readily appreciated by one skilled in the art. For example, while buffer concentrations can range from several millimolar up to the upper limit of their solubility, e.g., histidine could be as high as 200 mM, one skilled in the art would also take into consideration achieving/maintaining an appropriate physiologically suitable concentration. Percentages are weight/weight when referring to solids and weight/volume when referring to liquids. The term "isotonic," 300±50 mOsM, is meant to be a measure of osmolality of the protein solution prior to lyophilization; reconstitution is typically with water for injection (WFI). Maintaining physiological osmolality is important for the dosage formulations. However, for bulk formulations, much higher concentrations can be effectively utilized as long as the solution is made isotonic prior to use. The term "excipients" includes pharmaceutically acceptable reagents to provide good lyophilized cake properties (bulking agents) as well as provide lyoprotection and cryoprotection of the protein, maintenance of pH, and proper conformation of the protein during storage so that substantial retention of biological activity (protein stability) is maintained.

As used herein, factor IX concentration is conveniently expressed as mg/ml or as U/ml, with 1 mg approximately equal to 200 U/ml±100 U/ml.

The following examples illustrate practice of the invention. These examples are for illustrative purposes only and are not intended in any way to limit the scope of the invention claimed. Example 1 describes recombinant factor IX in various formulations (all isotonic), followed by lyophilization and storage at three different temperatures for one month. The compositions are reconstituted with water and evaluated for particulate formation, recovery of protein, specific activity, and percent aggregate formation. Example 2 provides further formulations and, Example 3 relates to bulk storage stability of factor IX at a relatively high protein concentration.

EXAMPLE 1

Samples are prepared in the formulations set forth in Table I below, at a recombinant factor IX protein concentration of ~0.5 mg/ml (100 U/ml) and an osmolality of 300±50 mOsM. All samples contain a recombinant form of factor IX as purified by conformation specific monoclonal antibody column. The preparation of recombinant factor IX has been described in U.S. Pat. No. 4,770,999, Kaufman, et al. One suitable purification method is that described in Hrinda, et al., Preclinical Studies of a Monoclonal Antibody—Purified Factor IX, Mononine™ Seminars in Hematology, 28(3):6(July 1991). Other methods of preparation include the use of conformation-specific monoclonal antibodies as described by Tharakan, et al., "Physical and biochemical properties of five commercial resins for immunoaffinity purification of factor IX." Journal of Chromatography 595:103–111 (1992); and by Liebman, et al., "Immunoaffinity purification of factor IX (Christmas factor) by using conformation-specific antibodies directed against the factor IX-metal complex." Proc. Nat'l. Acad. Sci., USA 82:3879–3883 (1985); as well as conventional chromatographic procedures, for example, as described by Hashimoto, et al., "A Method for Systematic Purification from Bovine Plasma of Six Vitamin K-Dependent Coagulation Factors: Prothrombin, Factor X, Factor IX, Protein C, and Protein Z." J. Biochem. 97:1347–1355 (1985), and Bajaj, P. et al. Prep. Biochem. 11:397 (1981).

TABLE I

| Sample Number | pH Buffer (10 mM) | Salt (Bulking agent) | Cryo-Lyo protectant |
|---|---|---|---|
| 1 | 7.0 histidine | 0.066M NaCl | 3% mannitol |
| 2 | 7.0 histidine | 0.13M glycine | 3% mannitol |
| 3 | 7.0 potassium phosphate | 0.12M glycine | 3% mannitol |
| 4 | 7.0 potassium phosphate | 0.25M glycine | 1% sucrose |
| 5 | 7.0 histidine | 0.26M glycine | 1% sucrose |
| 6 | 7.0 histidine | 0.25M glycine, 5 mM $Ca^{++}$ | 1% sucrose |
| 7 | 7.0 sodium phosphate | 0.25M glycine | 1% sucrose |
| 8 | 7.5 potassium phosphate | 0.25M glycine | 1% sucrose |

TABLE I-continued

| Sample Number | pH | Buffer (10 mM) | Salt (Bulking agent) | Cryo-Lyo protectant |
|---|---|---|---|---|
| 9 | 7.5 | sodium phosphate | 0.25M glycine | 1% sucrose |
| 10 | 7.5 | tris | 0.26M glycine | 1% sucrose |
| 11 | 7.5 | tris | 0.25M glycine, 5 mM $Ca^{++}$ | 1% sucrose |
| 12 | 7.5 | tris | 0.13M glycine | 3% mannitol |
| 13 | 7.5 | diethanolamine | 0.26M glycine | 1% sucrose |
| 14 | 7.5 | diethanolamine | 0.13M glycine | 3% mannitol |
| 15 | 7.5 | diethanolamine | 0.25M glycine, 5 mM $Ca^{++}$ | 1% sucrose |

Another set of 15 samples is prepared, as above however, containing, in addition, a surfactant, 0.005% Tween-80. The formulation of sample 1 is that formulation used for commercially available plasma-derived factor IX (Mononine™).

A. Effects of Freeze/Thaw Cycle

Prior to lyophilization, samples of each formulation are subjected to five freeze-thaw cycles to determine susceptibility to freezing-induced denaturation. A series of –80° C./37° C. freeze-thaw cycles (five, for example) prior to lyophilization is a useful "indication" of a protein's susceptibility to increased aggregate formation as may be observed in a lyophilization process and/or during long-term storage. Samples are assayed for the amount of "high molecular weight species" (HMW) present; HMW includes covalent and non-covalent aggregates as measured by SEC-HPLC and SDS-PAGE (reduced and non-reduced). Samples with Tween-80 (0.005%) added have minimal aggregation generated (less than 0.1% HMW increase). Without the addition of surfactant, formulations 1, 6, 11 and 15 show greater than 6% HMW generated and the other formulations had <4% HMW increase.

B. Temperature and Surfactant Effects Over Time

Prior to lyophilization, each sample (with and without surfactant (Tween (0.005%))) is sterile filtered through a 0.2 μm filter. Half ml volumes are filled into 2 ml lyophilization vials and loaded into a lyophilizer. The vials are frozen for 5.5 hours at –50° C. The shelf temperature is raised to –30° C. to begin primary drying and held for 42 hours. The shelf temperature is raised to +25° C. over a 1 hour time period, and secondary drying started and held for 15 hours. Vials are stoppered at the conclusion of secondary drying. All formulations exhibit good cake properties, and are all easily reconstituted in ≦30 seconds after water is added. Immediately after lyophilization, samples are evaluated for HMW increase. Most non-Tween containing had ~/–2% increase. Subsequently, samples are stored at three different temperatures (–80° C., 4° C., and 30° C.) for a one month period of time. The percentage HMW increase is expressed as a percent of area (absorbance at 280 nm) from SEC-HPLC after lyophilization. Table II. After one month storage, many non-surfactant-containing formulations give a higher percentage increase HMW ranging from 0 to 25%, which is most apparent at the 30° C. storage temperature. In particular, samples 1–3, 12, and 14 give the highest percentage increases.

While formulations having surfactant added, generally have a lower percentage increase in HMW, i.e., minimization of the freezing-induced aggregation from the lyophilization process itself, long-term lyoprotection further depends on the presence of other excipients. For example, those formulations with sucrose rather than mannitol have a lower percentage increase in HMW. Thus, mannitol formulations 1, 2, 3, 12 and 14, with or without surfactant, give up to a 36% increase in percent HMW.

TABLE II

SEC-HPLC Change in Percent HMW One Month At Three Temperatures Without Tween (–T) and With Tween (+T)

| Temp. Sample No. | Time Zero[1] | | –80° C. One Month[2] | | 4° C. One Month[2] | | 30° C. One Month[2] | |
|---|---|---|---|---|---|---|---|---|
| | –T | +T | –T | +T | –T | +T | –T | +T |
| 1 | 1.1 | 0.0 | 8.4 | –1.0 | 10.0 | –1.0 | 14.0 | 18.0 |
| 2 | 1.9 | 0.1 | 2.0 | 0.8 | 2.0 | 0.4 | 8.0 | 7.5 |
| 3 | 1.4 | 0.0 | 2.2 | 0.1 | 3.0 | –1.5 | 8.0 | 3.5 |
| 4 | 0.5 | 0.1 | 0.6 | –1.5 | 1.0 | –1.9 | 1.5 | –1.0 |
| 5 | 0.9 | 0.0 | 3.0 | –0.6 | 4.1 | –0.5 | 4.0 | –1.0 |
| 6 | 0.7 | 0.2 | 4.4 | 0.2 | 4.0 | 0.1 | 5.0 | 0.0 |
| 7 | 0.7 | 0.2 | 2.2 | –0.1 | 3.1 | –0.1 | 3.0 | –0.2 |
| 8 | 1.6 | 0.2 | 0.4 | –0.2 | 2.6 | –0.1 | 0.8 | –0.1 |
| 9 | 1.2 | 0.3 | 2.0 | –0.2 | 3.5 | –0.8 | 2.0 | –0.1 |
| 10 | 1.1 | 0.1 | 1.0 | –0.4 | 1.6 | –0.8 | 2.1 | –0.2 |
| 11 | 0.3 | 0.2 | 0.4 | 0.0 | 0.8 | –0.1 | 0.8 | 0.0 |
| 12 | 0.6 | 0.1 | 0.6 | –1.5 | 3.4 | –1.0 | 8.0 | 6.0 |
| 13 | 0.0 | 0.0 | 0.1 | 0.0 | 0.8 | –0.5 | 0.8 | 0.1 |
| 14 | 1.5 | 0.0 | 3.0 | 0.1 | 5.4 | 13.0 | 25.0 | 36.0 |
| 15 | 0.0 | 0.0 | –1.0 | 1.0 | –1.2 | 2.0 | 1.0 | 1.0 |

[1] = Time Zero (%) percent change in HMW from "before lyophilization" to "after lyophilization"
[2] = Increase in area % HMW relative to Time Zero value The clotting activity and specific activity values for the one month, –80° C., 4° C. and 30° C. samples are determined. Factor IX activity is determined according to the method of Pittman, D., et al., Blood 79:389–397 (1992) utilizing factor IX-deficient blood.

Little differences in recovery of activity or specific activity are observed at –80° C. or 4° C. after one month (with or without surfactant added); however, at 30° C., recovery of activity and specific activity correlates generally with the aggregation results; in other words, a loss of activity is generally observed with increased aggregation, most notably in formulations 1, 2, 3, 12, and 14, where addition of surfactant did not prevent aggregation from occurring over time.

EXAMPLE 2

Additionally, two formulations comprising histidine, glycine (with and without surfactant), and 2% sucrose, isotonic, are evaluated and are found to maintain factor IX activity.

Another set of 10 formulations is prepared as listed in Table III (with an osmolality of 300±50 mOsM), lyophilized as previously described, and placed at –80° C., 4° C., and 30° C. for storage and stability analysis at one, three, and four months. All samples have surfactant added, i.e., 0.005% Tween-80.

TABLE III

| Sample Number | pH | Buffer (10 mM) | Glycine | Sucrose % |
|---|---|---|---|---|
| 1 | 7.0 | histidine | 0.26M | 1 |
| 2 | 7.0 | histidine | 0.29M | 0 |
| 3 | 7.0 | sodium phosphate | 0.25M | 1 |
| 4 | 7.0 | potassium phosphate | 0.25M | 1 |
| 5 | 7.5 | tris | 0.26M | 1 |
| 6 | 7.5 | potassium phosphate | 0.25M | 1 |
| 7 | 7.5 | sodium phosphate | 0.25M | 1 |
| 8 | 7.0 | sodium phosphate | 0.29M | 0 |

TABLE III-continued

| Sample Number | pH | Buffer (10 mM) | Glycine | Sucrose % |
|---|---|---|---|---|
| 9 | 7.5 | sodium phosphate | 0.29M | 0 |
| 10 | 7.5 | tris | 0.29M | 0 |

All formulations form good lyophilized cakes and reconstitute within 20–30 seconds.

Table IV summarizes recovery of activity and specific activity after several months and at the three storage temperatures. The data for the 4° C. samples after three months is similar for most of the formulations except formulations 8 and 10 which lost activity. After three months, at 30° C., formulations 2, 8, 9, and 10 lost activity. The greatest recovery of activity and specific activity is seen for formulations 1, 3, 5, 6, and 7.

Table V summarizes increase in aggregation over time. At 4° C., after three months, formulations 1–7, have <4% increase in HMW, and at 30° C., formulations 8, 9, and 10 show highest aggregate formation. At 30° C., formulation 1 shows no increase in HMW, even after four months, with all the other formulations showing >3% HMW. Formulations 2, 8, 9, and 10 (all containing no sucrose) show elevated aggregate formation.

TABLE V-continued (%) HMW vs. Time Lyophilized

| | | 4° C. | | | 30° C. | | |
|---|---|---|---|---|---|---|---|
| Sample No. | Time Zero | 1 Month | 3 Months | 4 Months | 1 Month | 3 Months | 4 Months |
| 7 | 0.9 | 0.9 | 3.3 | ND | 1.9 | 4.2 | ND |
| 8 | 1.6 | 9.4 | 12.1 | ND | 16.0 | 18.6 | ND |
| 9 | 1.8 | 5.9 | 8.3 | ND | 20.0 | 34.5 | ND |
| 10 | 0.8 | 3.3 | 21.5 | ND | 76.0 | 72.0 | ND |

ND = not determined

EXAMPLE 3

To minimize the volume requirements of shipping containers, it is preferable to concentrate the bulk protein as much as possible (e.g., up to at least 20 mg/ml) prior to shipping to a fill/finish facility. Moreover, it is desirable to have the bulk drug product and finished product in similar formulations.

To evaluate concentrated preparations of factor IX, useful as bulk drug product, twelve formulations were prepared as indicated in Table VI below, except at high ($\geq 10$ mg/ml) factor IX concentrations. The surfactant concentration is either about 0.005 or 0.02% Tween-80 (useful as a Tween optimization study). All samples have factor IX at a concentration of $\geq 10$ mg/ml and sucrose at 1%. The osmolality of all samples was 300±50 mOsM.

TABLE IV

Percent Recovery of Activity/Specific Activity at Three Different Storage Temperatures and Times

TIME/TEMPERATURE

| | −80° C. | | | | | | 4° C. | | | | | | 30° C. | | | | | |
|---|---|---|---|---|---|---|---|---|---|---|---|---|---|---|---|---|---|---|
| | One Month | | 3 Months | | 4 Months | | One Month | | 3 Months | | One Month | | 3 months | | 4 Months | | | |
| Sample Number | Act. | Spec. Act. | Act. | Spec. Act. | Act. | Spec. Act. | Act. | Spec. Act. | Act. | Spec. Act. | Act. | Spec. Act. | Act. | Spec. Act. | Act. | Spec. Act. | | |
| 1 | 100 | 92 | 103 | 92 | 100 | 99 | 110 | 110 | 110 | 109 | 100 | 100 | 100 | 97 | 93 | 95 | | |
| 2 | 100 | 90 | 98 | 100 | ND | ND | 104 | 108 | 83 | 88 | 54 | 55 | 44 | 52 | ND | ND | | |
| 3 | 112 | 110 | 90 | 90 | 92 | 89 | 105 | 108 | 97 | 102 | 99 | 100 | 85 | 95 | 89 | 90 | | |
| 4 | 85 | 90 | 85 | 84 | ND | ND | 91 | 95 | 81 | 90 | 84 | 92 | 58 | 64 | ND | ND | | |
| 5 | 94 | 96 | 99 | 95 | 95 | 90 | 92 | 96 | 107 | 106 | 85 | 90 | 83 | 92 | 80 | 78 | | |
| 6 | 100 | 102 | 96 | 100 | ND | ND | 100 | 102 | 92 | 100 | 91 | 96 | 77 | 85 | ND | ND | | |
| 7 | 100 | 102 | 100 | 100 | ND | ND | 110 | 110 | 100 | 112 | 111 | 115 | 86 | 97 | ND | ND | | |
| 8 | 105 | 105 | 92 | 94 | ND | ND | 78 | 90 | 64 | 72 | 50 | 70 | 0 | ND | ND | ND | | |
| 9 | 110 | 110 | 94 | 98 | ND | ND | 100 | 102 | 84 | 94 | 48 | 60 | 26 | 41 | ND | ND | | |
| 10 | 90 | 90 | 84 | 80 | ND | ND | 70 | 85 | 21 | 26 | 0 | 0 | 0 | ND | ND | ND | | |

All percentages are expressed as a percentage of the Time Zero, which in this case is "Post-lyophilization" and is set equal to 100%. Recoveries greater than 100% reflect assay variability.
Spec. Act. = Specific Activity (U/mg)
Act. = Activity (U/ml) = Clotting Activity
ND = not determined

TABLE V (%) HMW vs. Time Lyophilized

| | | 4° C. | | | 30° C. | | |
|---|---|---|---|---|---|---|---|
| Sample No. | Time Zero | 1 Month | 3 Months | 4 Months | 1 Month | 3 Months | 4 Months |
| 1 | 0.6 | 0.1 | 0.0 | 0.1 | 0.1 | 0.2 | 0.3 |
| 2 | 0.6 | 0.1 | 0.5 | ND | 2.8 | 6.3 | ND |
| 3 | 0.5 | 0.5 | 1.4 | 1.8 | 1.0 | 3.5 | 4.0 |
| 4 | 0.6 | 0.6 | 1.9 | ND | 1.2 | 3.9 | ND |
| 5 | 0.5 | 0.0 | 0.3 | 1.2 | 0.4 | 3.0 | 5.1 |
| 6 | 0.6 | 0.7 | 2.6 | ND | 1.4 | 4.7 | ND |

TABLE VI

Factor IX Formulations - Bulk High Concentration

| Sample No. | pH | Buffer (10 mM) | Salts | % Tween-80 |
|---|---|---|---|---|
| 1A | 7.0 | histidine | 0.26 M glycine | .005 |
| 1B | 7.0 | histidine | 0.26 M glycine | .02 |
| 2A | 7.0 | sodium phosphate | 0.25 M glycine | .005 |
| 2B | 7.0 | sodium phosphate | 0.25 M glycine | .02 |

TABLE VI-continued

Factor IX Formulations - Bulk High Concentration

| Sample No. | pH | Buffer (10 mM) | Salts | % Tween-80 |
|---|---|---|---|---|
| 3A | 7.0 | potassium phosphate | 0.25 M glycine | .005 |
| 3B | 7.0 | potassium phosphate | 0.25 M glycine | .02 |
| 4A | 7.5 | tris | 0.26 M glycine | .005 |
| 4B | 7.5 | tris | 0.26 M glycine | .02 |
| 5A | 7.5 | potassium phosphate | 0.25 M glycine | .005 |
| 5B | 7.5 | potassium phosphate | 0.25 M glycine | .02 |
| 6A | 7.5 | sodium phosphate | 0.25 M glycine | .005 |
| 6B | 7.5 | sodium phosphate | 0.25 M glycine | .02 |

The samples are subjected to five freeze-thaw cycles, repeated freezing at −80° C., subsequent thawing at 37° C. for five cycles, and analyzed for recovery of total factor IX concentration, activity, and specific activity. The level of factor IX (mg/ml) ranges from 10.40 to 15.20 mg/ml. The initial percent HMW is <0.5%. There is no loss of protein or activity, and no significant increase in aggregate formation from the freeze-thaw cycles for the 12 formulations. The high concentration formulated bulk product for several formulations of Table V are analyzed for stability after storage at −80° C. for one month. No increase in % HMW is observed and the specific activity is maintained.

While the present invention has been described in terms of specific methods, formulations, and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A lyophilized composition comprising factor IX, glycine, polysorbate, sucrose and histidine.

2. The composition of claim 1, wherein the concentration of said glycine is about 0.1 to 0.3 M.

3. The composition of claim 1, wherein the concentration of said glycine is about 0.2 to 0.3 M.

4. The composition of claim 1, wherein the concentration of said glycine is about 0.26 M.

5. The composition of claim 1, wherein the concentration of said polysorbate is about 0.005 to 0.05%.

6. The composition of claim 1, wherein the concentration of said polysorbate is about 0.005%.

7. The composition of claim 1, wherein the concentration of said sucrose is about 0.5 to 2%.

8. The composition of claim 1, wherein the concentration of said sucrose is about 1%.

9. The composition of claim 1, wherein the concentration of said histidine is about 5 to 30 mM.

10. The composition of claim 1, wherein the concentration of said histidine is about 10 mM.

11. A lyophilized composition comprising about 0.4 to 20 mg/ml factor IX, about 0.1 to 0.3 M glycine, about 0.5 to 2% sucrose, about 0.005 to 0.05% polysorbate and about 5 to 30 mM histidine.

12. A lyophilized composition comprising 0.75 mg/ml factor IX, 0.26 M glycine, 10 mM histidine, 1% sucrose and 0.005% polysorbate.

* * * * *